(12) United States Patent
Filimonov et al.

(10) Patent No.: US 12,376,766 B2
(45) Date of Patent: Aug. 5, 2025

(54) SYSTEM AND METHOD FOR DETERMINING HEART BEAT FEATURES

(71) Applicant: Harman Becker Automotive Systems GmbH, Karlsbad (DE)

(72) Inventors: Andrey Viktorovich Filimonov, Kamenki (RU); Ivan Sergeevich Shishalov, Nizhniy Novgorod (RU); Roman Aleksandrovich Ershov, Nizhny Novgorod (RU); Andrey Sergeevich Shilov, Nizhny Novgorod (RU)

(73) Assignee: HARMAN BECKER AUTOMOTIVE SYSTEMS GMBH, Karlsbad (DE)

( * ) Notice: Subject to any disclaimer, the term of this patent is extended or adjusted under 35 U.S.C. 154(b) by 760 days.

(21) Appl. No.: 17/451,470

(22) Filed: Oct. 19, 2021

(65) Prior Publication Data

US 2022/0117517 A1    Apr. 21, 2022

(30) Foreign Application Priority Data

Oct. 19, 2020 (WO) ................ PCT/RU2020/000555

(51) Int. Cl.
*A61B 5/1171* (2016.01)
*A61B 5/00* (2006.01)
(Continued)

(52) U.S. Cl.
CPC .......... *A61B 5/1176* (2013.01); *A61B 5/0077* (2013.01); *A61B 5/02108* (2013.01);
(Continued)

(58) Field of Classification Search
CPC ..... A61B 5/02; A61B 5/1176; A61B 5/02416; A61B 5/024
See application file for complete search history.

(56) References Cited

U.S. PATENT DOCUMENTS 6,090,051 A    7/2000   Marshall
6,102,870 A    8/2000   Edwards
(Continued)

FOREIGN PATENT DOCUMENTS

CN    112052830 A  * 12/2020  ......... G06K 9/00228
CN    111611905 B  *  4/2023  ......... G06K 9/00671
(Continued)

OTHER PUBLICATIONS

European Patent Office, Extended European Search Report Issued in Application No. 21203425.0, Mar. 9, 2022, Germany, 5 pages.
(Continued)

*Primary Examiner* — Christopher Koharski
*Assistant Examiner* — Younhee Choi
(74) *Attorney, Agent, or Firm* — McCoy Russell LLP (57) ABSTRACT

Method for determining one or more heart beat features, the method comprising: capturing a series of visible light images of a face of a user by a visible light camera; capturing, during capturing the series of the visible light images, at least one infrared image of the face by an infrared camera; detecting, on the at least one infrared image, one or more first face landmarks indicative of a location of the face; locating one or more skin patches on the visible light image series; and determining one or more heart beat features based on the skin patches; characterized in that locating one or more skin patches comprises determining a position of the skin patches relative to the one or more first face landmarks.

10 Claims, 4 Drawing Sheets

(51) Int. Cl.
    *A61B 5/021*     (2006.01)
    *A61B 5/024*     (2006.01)
    *A61B 5/026*     (2006.01)
    *A61B 5/18*     (2006.01)

(52) U.S. Cl.
    CPC .......... *A61B 5/02405* (2013.01); *A61B 5/026* (2013.01); *A61B 5/18* (2013.01)

(56) References Cited

U.S. PATENT DOCUMENTS

| | | | |
|---|---|---|---|
| 6,496,594 | B1* | 12/2002 | Prokoski .............. A61B 5/415 382/125 |
| 7,344,251 | B2 | 3/2008 | Marshall |
| 7,435,227 | B2 | 10/2008 | Farbos |
| 7,438,418 | B2 | 10/2008 | Marshall |
| 7,938,785 | B2 | 5/2011 | Aguilar et al. |
| 8,977,347 | B2 | 3/2015 | Mestha et al. |
| 9,642,536 | B2 | 5/2017 | Kashef et al. |
| 9,646,046 | B2 | 5/2017 | Sadowsky et al. |
| 9,723,992 | B2 | 8/2017 | Senechal et al. |
| 9,763,573 | B2 | 9/2017 | Distasi et al. |
| 9,934,425 | B2 | 4/2018 | el Kaliouby et al. |
| 10,111,611 | B2 | 10/2018 | el Kaliouby et al. |
| 10,667,723 | B2 | 6/2020 | Jacquel et al. |
| 2007/0066916 | A1 | 3/2007 | Lemos |
| 2008/0150734 | A1 | 6/2008 | Johns |
| 2014/0316293 | A1* | 10/2014 | Ahmad .................. A61B 5/024 600/508 |
| 2015/0297142 | A1* | 10/2015 | De Jaam .............. G06V 10/143 600/407 |
| 2016/0228069 | A1 | 8/2016 | Derkx et al. |
| 2018/0055391 | A1 | 3/2018 | Murakami et al. |
| 2018/0096119 | A1* | 4/2018 | Yun ........................ A61B 5/024 |
| 2018/0125356 | A1 | 5/2018 | Yamada |
| 2018/0125405 | A1 | 5/2018 | Yamada |
| 2018/0125406 | A1 | 5/2018 | Yamada |
| 2018/0153422 | A1* | 6/2018 | Watanabe .............. A61B 6/563 |
| 2019/0350471 | A1 | 11/2019 | Marks et al. |
| 2020/0214614 | A1 | 7/2020 | Rundo et al. |

FOREIGN PATENT DOCUMENTS

| | | |
|---|---|---|
| WO | 2006024129 A1 | 3/2006 |
| WO | 2008107832 A1 | 9/2008 |
| WO | 2015116832 A1 | 8/2015 |

OTHER PUBLICATIONS

Malik, M. et al., "Heart rate variability and clinical cardiology," British Heart Journal, vol. 71, No. 1, Jan. 1994, 4 pages.
Carney, R. et al., "Change in Heart Rate and Heart Rate Variability During Treatment for Depression in Patients with Coronary Heart Disease," Psychosomatic Medicine, vol. 62, No. 5, Sep. 2000, 9 pages.
"Driver Workload Metrics Project—Task 2 Final Report," NHTSA Website, Available Online at https://www.nhtsa.gov/document/driver-workload-metrics-project-task-2-final-report, Nov. 2006, 460 pages.
Sforza, E. et al., "Cardiac Variability and Heart-Rate Increment as a Marker of Sleep Fragmentation in Patients With a Sleep Disorder: a Preliminary Study," Sleep, vol. 30, No. 1, Jan. 2007, 9 pages.
Patil, S. et al., "Extraction of Significant Patterns from Heart Disease Warehouses for Heart Attack Prediction," IJCSNS International Journal of Computer Science and Network Security, vol. 9, No. 2, Feb. 2009, 8 pages.
Estrada, E. et al., "EEG and HRV Signal Features for Automatic Sleep Staging and Apnea Detection," Proceedings of the 2010 20th International Conference on Electronics Communications and Computers (CONIELECOMP), Feb. 22, 2010, Cholula, Puebla, Mexico, 6 pages.
Mohebbi, M. et al., "Prediction of paroxysmal atrial fibrillation based on non-linear analysis and spectrum and bispectrum features of the heart rate variability signal," Computer Methods and Programs in Biomedicine, vol. 105, No. 1, Jan. 2012, Available Online Aug. 21, 2010, 10 pages.
Huikun, H,et al., "Heart Rate Variability in Risk Stratification of Cardiac Patients," Progress in Cardiovascular Diseases, vol. 56, No. 2, Sep. 2013, Available Online Aug. 12, 2013, 7 pages.
Tobaldini, E. et al., "Heart rate variability in normal and pathological sleep," Frontiers in Physiology, vol. 4, No. 294, Oct. 16, 2013, 12 pages.
Moon, E. et al., "Comparative Study of Heart Rate Variability in Patients with Schizophrenia, Bipolar Disorder, Post-traumatic Stress Disorder, or Major Depressive Disorder," Clinical Psychopharmacology and Neuroscience, vol. 11, No. 3, Dec. 2013, 7 pages.
Ebrahimzadeh, E. et al., "A Novel Approach to Predict Sudden Cardiac Death (SCD) Using Nonlinear and Time-Frequency Analyses from HRV Signals," PLOS ONE, vol. 9, No. 2, Feb. 4, 2014, 14 pages.
Li, X. et al., "Remote Heart Rate Measurement From Face Videos Under Realistic Situations," Proceedings of the 2014 IEEE Conference on Computer Vision and Pattern Recognition, Jun. 23, 2014, Columbus, Ohio, 8 pages.
Wang, W. et al., "Exploiting Spatial Redundancy of Image Sensor for Motion Robust rPPG," IEEE Transactions on Biomedical Engineering, vol. 62, No. 2, Feb. 2015, 11 pages.
Rubin, J. et al., "Towards a Mobile and Wearable System for Predicting Panic Attacks," UbiComp '15: Proceedings of the 2015 ACM International Joint Conference on Pervasive and Ubiquitous Computing, Sep. 7, 2015, Osaka, Japan, 5 pages.
Lam, A. et al., "Robust Heart Rate Measurement from Video Using Select Random Patches," Proceedings of the 2015 IEEE International Conference on Computer Vision (ICCV), Dec. 7, 2015, Santiago, Chile, 9 pages.
Fujiwara, K. et al., "Epileptic Seizure Prediction Based on Multivariate Statistical Process Control of Heart Rate Variability Features," IEEE Transactions on Biomedical Engineering, vol. 63, No. 6, Jun. 2016, 11 pages.
Koenig, J. et al., "Depression and resting state heart rate variability in children and adolescents—A systematic review and meta-analysis," Clinical Psychology Review, vol. 46, Jun. 2016, 15 pages.
Wang, W. et al., "A Novel Algorithm for Remote Photoplethysmography: Spatial Subspace Rotation," IEEE Transactions on Biomedical Engineering, vol. 63, No. 9, Sep. 2016, 11 pages.
Monkaresi, H. et al., "Automated Detection of Engagement using Video-Based Estimation of Facial Expressions and Heart Rate," IEEE Transactions on Affective Computing, vol. 8, No. 1, Jan. 1, 2017, 14 pages.
Wang, W. et al., "Algorithmic Principles of Remote-PPG," IEEE Transactions on Biomedical Engineering, vol. 64, No. 79, Jul. 2017, 12 pages.
Hassan, M. et al., "Heart rate estimation using facial video: A review," Biomedical Signal Processing and Control, vol. 38, Sep. 2017, 15 pages.
Myers, K. et al., "Heart rate variability in epilepsy: A potential biomarker of sudden unexpected death in epilepsy risk," Epilepsia, vol. 59, No. 7, Jun. 6, 2018, 9 pages.
Balakrishnan, G. et al., "Detecting Pulse from Head Motions in Video," Proceedings of the 2013 IEEE Conference on Computer Vision and Pattern Recognition, Jun. 23, 2018, Portland, Oregon, 8 pages.
Chen, Z. et al., "Estimating Depth from RGB and Sparse Sensing," Proceedings of the European Conference on Computer Vision (ECCV), Sep. 8, 2018, Munich, Germany, 16 pages.
"European New Car Assessment Programme (Euro NCAP) Assessment Protocol—Adult Occupant Protection," Euro NCAP Website, Available Online at https://cdn.euroncap.com/media/43372/euro-ncap-assessment-protocol-aop-v901.pdf, Feb. 2019, 50 pages.
Harford, M. et al., "Availability and performance of image-based, non-contact methods of monitoring heart rate, blood pressure, respiratory rate, and oxygen saturation: a systematic review," Physiological Measurement, vol. 40, No. 6, Jul. 3, 2019, 18 pages.

* cited by examiner

Fig. 4 ial Patent Application No. PCT/RU2020/000555...

SYSTEM AND METHOD FOR DETERMINING HEART BEAT FEATURES

CROSS-REFERENCE TO RELATED APPLICATIONS

The present application claims priority to International Patent Application No. PCT/RU2020/000555, entitled "SYSTEM AND METHOD FOR DETERMINING HEART BEAT FEATURES," and filed on Oct. 19, 2020. The entire contents of the above-listed application is hereby incorporated by reference for all purposes.

FIELD

The present disclosure relates to systems and methods for monitoring the health of a person, in particular to determining heart beat features, such as a heart rate.

BACKGROUND

Measuring heart beat features of a driver of a vehicle, in particular, a heart interbeat interval, or a heart rate, can be useful in order to monitor the health of a driver, and in order to detect the driver's mental state. For example, a driver experiencing stress may be paying less attention to the traffic. Known contactless optical blood flow measurement techniques are configured to operate when sufficient lighting is available, and when conditions are stable over time. Therefore, a need exists for a blood flow measurement technique that is configured for operation at less bright illumination and in noisy environments.

The following publications relate to applications of the present disclosure:
Koenig et al., Clin. Psych. Rev. 46, 136 (2016) DOI: 10.1016/j.cpr.2016.04.013
Tobaldini et al., Front. Physiol. 4, 294 (2013) DOI: 10.3389/fphys.2013.00294
Sforza et al., Sleep 30, 43 (2007), DOI: 10.1093/sleep/30.1.43
Moon et al., Clin. Psychopharmacol. Neurosci. 11, 137 (2013) DOI: 10.9758/cpn.2013.11.3.137
Carney et al., Psychosomat. Medicine 62, 639 (2000)
Estrada et al., 20th International Conference on Electronics Communications and Computers, 142 (2010) DOI: 10.1109/CONIELECOMP.2010.5440778
Fujiwara et al., IEEE Trans. Biomedical Engin. 63, 1321 (2016), DOI:10.1109/TBME.2015.2512276
Myers et al., Epilepsia 59, 1372 (2018) DOI: 10.1111/epi.14438
Rubin et al., Proc. 2015 ACM Internat. Joint Conf. Pervasive and Ubiquitous Computing, 529 (2015), DOI: 10.1145/2750858.2805834
Ebrahimzadeh et al., PLoS ONE 9, e81896 (2014) DOI: 10.1371/journal.pone.0081896
Malik et al., Br. Heart J 71, 3 (1994)
Huikuri et al., Progr. Cardiovascular Diseases 56, 153 (2013)
Mohebbi et al., Comput. Meth. Progr. Biomed. 105, 40 (2012), DOI: 10.1016/j.cmpb.2010.07.011
Patil et al., Internat. J. Comput. Sci. Netw. Sec. 9, 228 (2009)
NTHSA: Driver Workload Metrics Project (2006)
Euro NCAP Assessment Protocol, v 9.0.1 (2019)
The following publications relate to detecting a mental state using a heart rate:
U.S. Pat. No. 9,934,425B2
US20180125405A1
US20180125356A1
U.S. Pat. No. 7,344,251B2
U.S. Pat. No. 6,090,051A
US20180125406A1
U.S. Pat. No. 7,435,227B2
U.S. Pat. No. 7,938,785B2
WO2006024129A1
U.S. Pat. No. 9,723,992B2
U.S. Pat. No. 9,646,046B2
U.S. Ser. No. 10/111,611B2
U.S. Pat. No. 9,763,573B2
WO2015116832A1
U.S. Pat. No. 7,438,418B2
US20070066916A1
WO2008107832A1
U.S. Pat. No. 6,102,870A
US20080150734A1
The following publications relate to remote heart rate detection:
U.S. Ser. No. 10/667,723B2
US20160228069A1
U.S. Pat. No. 8,977,347B2
U.S. Pat. No. 9,642,536B2
Monkaresi et al., IEEE Transactions on Affective Computing 8, 1 (2016)
Balakrishnan et al., Proc. IEEE Conf. Computer Vision and Pattern Recognition 3040 (2013), DOI: 10.1109/CVPR.2013.440
Hassan et al., Biomedical Signal Processing and Control 38, 346 (2017)
Chen et al., Proc. European Conference on Computer Vision (2018)
Harford et al., Physiological Measurement 40, 6 (2019), DOI: 10.1088/1361-6579/ab1f1
Lam et al., 2015 IEEE International Conference on Computer Vision 3640 (2015), DOI: 10.1109/ICCV.2015.415
Li et al., 2014 IEEE Conference on Computer Vision and Pattern Recognition 4321 (2014), DOI: 10.1109/CVPR.2014.543
Wang et al., IEEE Transactions on Biomedical Engineering 62, 415 (2015). DOI: 10.1109/TBME.2014.2356291
Wang et al., IEEE transactions on Biomedical Engineering 63, 1964 (2015). DOI: 10.1109/TBME.2015.2508602
Wang et al., IEEE Transactions on Biomedical Engineering 64, 1479 (2017). DOI: 10.1109/TBME.2016.2609282

SUMMARY

A first aspect of the present disclosure relates to a method for determining one or more heart beat features. The method comprises:
    capturing a series of visible light images of a face of a user by a visible light camera;
    capturing, during capturing the series of the visible light images, at least one infrared image of the face by an infrared camera;
    detecting, on the at least one infrared image, one or more first face landmarks indicative of a location of the face;
    locating one or more skin patches on the visible light image series; and
    determining one or more heart beat features based on the skin patches.

According to the present disclosure, locating one or more skin patches comprises determining a position of the skin patches relative to the one or more first face landmarks.

The objective of the method is to determine heart beat features by remote photoplethysmography (rPPG), based on the visible light images of the skin patches of the user's face. If the user moves his head from time to time, the location of the skin patches that are useful for rPPG changes. Therefore, the method comprises locating the skin patches by detecting face landmarks, e. g. positions of facial features such as borders and corners of eyebrows, eyes, nose, mouth, and other parts of the face. The method further comprises determining the heart beat features, e. g. a heart rate, based on the skin patches, by rPPG. In some cases, the lighting conditions are poor, for example when only natural lighting is available. Then, the visible light camera cannot be relied upon for detecting the landmark positions, although the lighting is still sufficient for determining the heart beat features by rPPG. Since in the infrared spectrum, the lighting conditions may be sufficient, the infrared images are used to determine the skin patch locations. Therefore, the infrared images should be recorded at approximately the same time as the visible light images. A small delay from exact synchronization, however, is permissible if it happens on a timescale that still allows detecting the position of the head, i. e. either because the timescale is much smaller than the timescale at which the user can move his head, or because a plurality of visible light and infrared images are recorded, and values are interpolated.

In an embodiment, the method further comprises detecting, on at least one of the visible light images, one or more second face landmarks indicative of a location of the face. In said embodiment, locating the skin patches comprises determining a position of the skin patches relative to the one or more second face landmarks if a confidence value indicates equal or higher confidence for the second face landmarks. Thereby, both camera images —visible and infrared light images—are used to determine face landmarks, and the most reliable source of face landmarks is chosen according to the current conditions. If for example, the view for the infrared camera is blocked, the visible light camera is used both for locating the skin patches and for determining the heart beat features.

In a further embodiment, the confidence value is indicative of the confidence of the second face landmarks on a visible light image relative to the confidence of the first face landmarks on an infrared image. This allows deciding on whether to rely on the infrared image or on the visible light image on an image-to-image basis. However, the decision on whether to use the first face landmarks or the second face landmarks may depend, in addition or alternatively, on in other factors, such as brightness and contrast of the images of both cameras.

In a further embodiment, the confidence value is indicative of the confidence of the second face landmarks on a sequence of visible light images relative to the confidence of the first face landmarks on a sequence of infrared images. Thereby, fluctuations in the confidence value are smoothed out so that they do not lead the system to switch forth and back between both sources of landmarks. This is particularly useful if there are small differences in the way the camera positions are calibrated, as detailed below.

In a further embodiment, the method further comprises transforming the first face landmarks into a reference frame of the visible light camera. The first face landmarks are determined using the images of the infrared camera, wherein a sensor records a physical image of the face, as generated with an imaging optics comprised in the infrared camera. Therefore, the face landmark positions may be recorded as positions of the face landmark, e. g. the tip of the nose, on the image on the camera sensor. The first face landmark may thus be recorded as a pixel position, e. g. in a line/row format. Similarly, the second face landmarks may be recorded as pixel positions of the image of the same landmark on the visible light camera's sensor. Since the cameras are located at different positions and/or observe the face at different angles, the pixel positions of the same landmark of the same face recorded at the same time are in general not identical. Therefore, the cameras have different reference frames that define a different relation between the actual position of the face landmark and the position on the image. In order to facilitate determining the locations of the skin patches on a visible light image based on face landmark positions determined from an infrared image, the positions may therefore be transformed into a reference frame of the visible light camera. Subsequently, the skin patches may be located by the same algorithm that locates the skin patches based on the face landmarks as determined using the visible light camera. Such an algorithm may select an area at a predetermined position relative to the face landmarks for analysis, for example the area around the eyes, which is particularly useful for determining the heart beat features by remote rPPG. The software may thus have a modular configuration.

In a further embodiment, determining one or more heart beat features comprises determining a blood flow intensity value. On the image recorded by the visual light camera, a pixel, or a zone comprising a plurality of pixels, of which the position has been determined, is analyzed as a function of time, i. e. the change of the value in subsequent frames is determined and recorded. In particular, this analysis can be done to a color channel if the visual light camera is an red-green-blue (RGB) color camera. This allows selecting the color channel that varies most with the blood flow.

In a further embodiment, determining one or more heart beat features comprises determining a blood pulse wave. A blood pulse wave a pressure wave of the blood, generated by the heart beat, that propagates through the blood vessels. The blood pulse wave is measured as blood pressure intensity over time by detecting the increase in volume of the blood vessels that is indicated by the blood flow intensity value, by rPPG.

In a further embodiment, determining one or more heart beat features comprises determining one or more of a heart inter-beat interval, a heart rate, and a heart rate variability. Determining said features may comprise determining one or more peaks of the blood pulse wave. Other procedures for determining periodic processes, such as Fourier transformation and Wavelet transformations, may be additionally used.

In a further embodiment, detecting one or more first face landmarks comprises:
  detecting, on a first infrared image, one or more first preliminary face landmarks;
  detecting, on a second infrared image recorded before or after the first infrared image, one or more second preliminary face landmarks; and
  determining the one or more first face landmarks by interpolating between the first preliminary face landmarks and the second preliminary face landmarks.

Thereby, the first face landmarks are determined by an interpolation in time between two infrared images. This is beneficial if the infrared camera and the visible light camera are not synchronized in time, for example if the frame rates of the cameras differ. For each visible light image, preliminary face landmarks may be determined on a first infrared image recorded immediately before recording the visible light image, and a second infrared image recorded immediately after recording the visible light image. Interpolating between the preliminary face landmarks then allows determining the position at the moment when the visible light image was taken. A linear interpolation may be used, e. g. by a weighted average, wherein the weights correspond to the delays between visible light image and infrared image recording.

In a further embodiment, a frame rate of the visible light camera is equal to a frame rate of the infrared camera. A typical value of a frame rate may be, for example, 30 frames per second. Having both cameras record the images at the same frame rate facilitates mapping each infrared image to a visible light image, so that the first face landmarks can be used together with a visible light image that was recorded at approximately the same time. Thereby, the correspondence of the images is improved even if the user is quickly moving his head.

In a further embodiment, capturing the series of visible light images is synchronized in time to capturing the one or more infrared images. Full synchronization further improved the correspondence of the images.

In a further embodiment, the method further comprises illuminating the face with an infrared light source while capturing the one or more infrared images. The infrared light source may comprise a lamp, a light-emitting diode, or another source of infrared radiation. The infrared light source may provide constant illumination or a flash. The illumination in the infrared spectrum improves the detection of the first face landmarks by the infrared camera. As infrared light is invisible to the human eye, the user is not distracted by the light source. This is an advantage, for example, when the user has to perform tasks in a dark environment, such as driving a car at dusk.

In a further embodiment, the visible light camera and the infrared camera are attached to or comprised in a vehicle. This allows determining the heart rate of a driver or a passenger of a vehicle. Thereby, the health of the user can be monitored when driving, thereby benefiting from the availability of the user for measurements without the user unduly investing time into health monitoring. Monitoring the health of a driver allows, for example, generating an output signal to invite the driver to stop the car, in case of acute health problems.

In a further embodiment, the method further comprises detecting, based on the one or more heart beat features, cognitive load, stress, or drowsiness of a user of a system corresponding to the present disclosure. This allows determining if the driver of a vehicle is likely to drive safely and to pay attention to the traffic.

According to a second aspect of the disclosure, a system for determining one or more heart beat features is provided. The system comprises a visible light camera, an infrared camera, and a computing device. The system is configured to execute the steps described above. All properties of the method of the present disclosure also apply to the system.

BRIEF DESCRIPTION OF THE DRAWINGS

The features, objects, and advantages of the present disclosure will become more apparent from the detailed description set forth below when taken in conjunction with the drawings in which like reference numerals refer to similar elements.

DETAILED DESCRIPTION OF THE PREFERRED EMBODIMENTS

Figure 1:
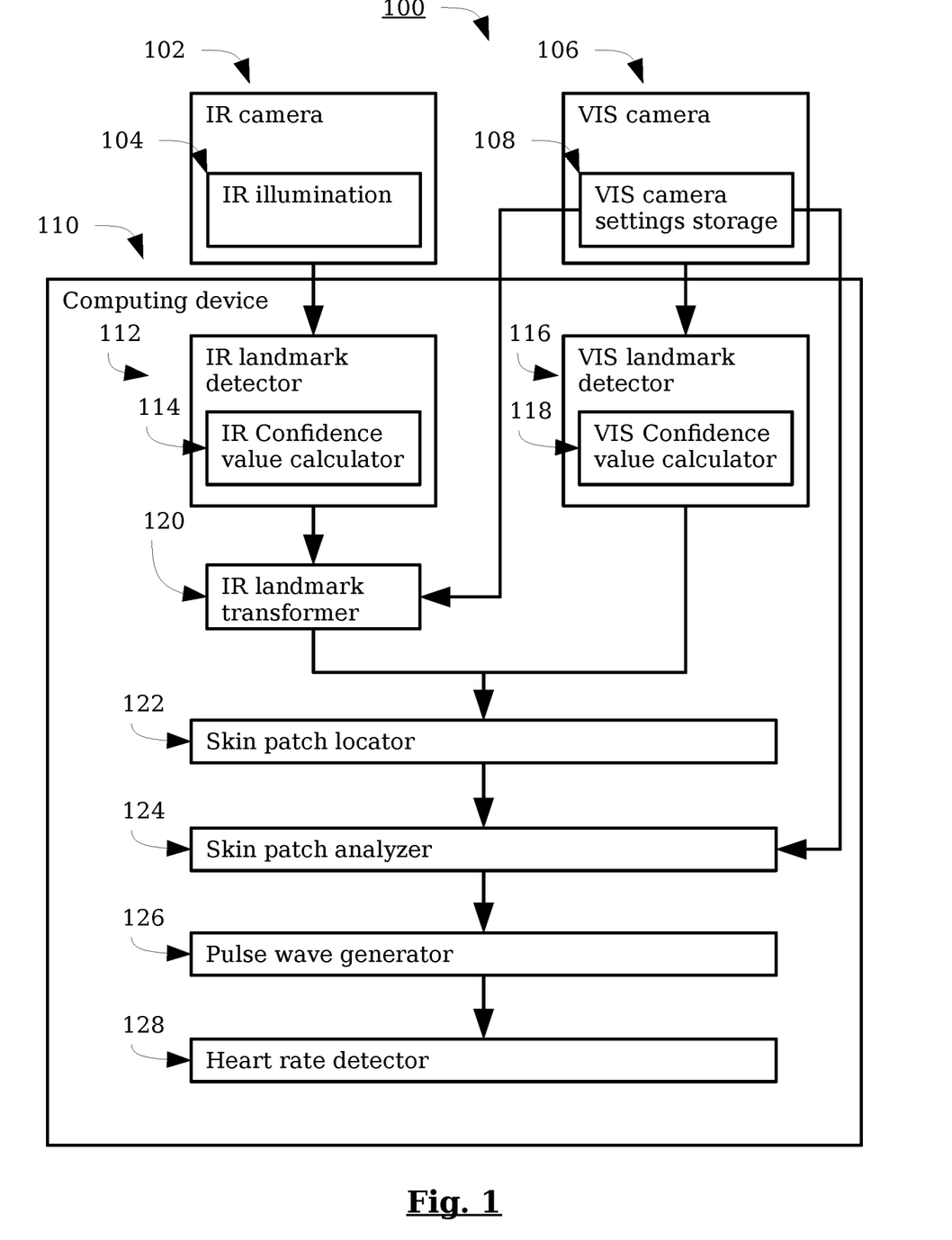
FIG. 1 depicts a block diagram of a system 100 for locating one or more skin patches according to an embodiment.

FIG. 1 depicts a block diagram of a system 100 for locating one or more skin patches according to an embodiment. The system comprises an infrared camera (IR camera) 106, and a camera 102 for visible light (VIS camera). Both cameras face the user of the system, and record images of the user's face. Typical frame rates for the cameras may be, e. g., between 30 frames per second (fps) and 60 fps. The camera resolutions for the infrared camera are high enough to allow recognizing facial contours and features, such as the locations of eyes, eyebrows, nose, and mouth. A typical value may be 1280 px×800 px, for example. The IR camera 102 may further comprise an IR illumination device 104, such as a flash, a lamp, or a light emitting diode, to illuminate the face of the user.

The RGB camera further comprises, e. g. as part of a control unit, a settings storage 108. The settings storage 108 is configured to store information on the color channels, as well as information on the RGB camera's and IR camera's relative positions. However, in another exemplary embodiment, these data may be stored elsewhere, for example in the computing device 110, as described below.

The data from the cameras and/or other sensors are processed by a computing device 110. The components 112-128 of the computing device 110 may be implemented in hardware or in software. The images of both cameras 102, 106, are analyzed to determine face landmarks. This analysis may be based on the same method, but different analysis methods may be used. Possible systematic differences between the analysis methods may be taken into account by the IR landmark transformer 120 described below. The face landmarks are generated by the landmark detectors 112, 116, and are indicative of the face location. They represent positions of parts of the face, such as a contour of a chin, an eyebrow, etc. Furthermore, for the face landmarks, a confidence value is generated, by the two confidence value calculators 114, 118. The confidence values reflect the probability that the landmarks are accurate. They are expressed on the same scale and therefore comparable. The first landmarks, determined by the IR landmark detector 112, are then fed into an IR landmark transformer 120 to transform the landmarks into a reference frame of the VIS camera 106. Transforming the landmarks corrects the landmark positions in order to account for the different positions and angles at which the cameras are located. Transforming may also account for systematic differences between the analysis methods used by the landmark detectors 112, 116. The skin patch locator 122 then chooses the set of landmarks, either from the IR image or the VIS image, with the higher confidence values. The positions of the skin patches are then determined as relative positions to the face landmarks. The skin patch analyzer 124 determines the color channel of the pixels from the VIS camera that exhibits the strongest dependence on the blood pulse wave. The choice of a color channel may be predetermined, or it may be chosen during operation, e. g. based on a contrast value of a pulse wave, or on an intensity value of a Fourier or wavelet transform corresponding to the range of typical human heart rates.

Analysis may be based on single pixels, or on zones comprising a plurality of pixels. For each pixel or zone, the skin patch analyzer 124 yields a time series of values obtained from a series of VIS camera images. The pulse wave generator 126 then uses these values to determine the pulse wave by rPPG. The Heart rate detector 128 detects the periodicity in the blood pulse wave and detects a heart rate.

Figure 2:
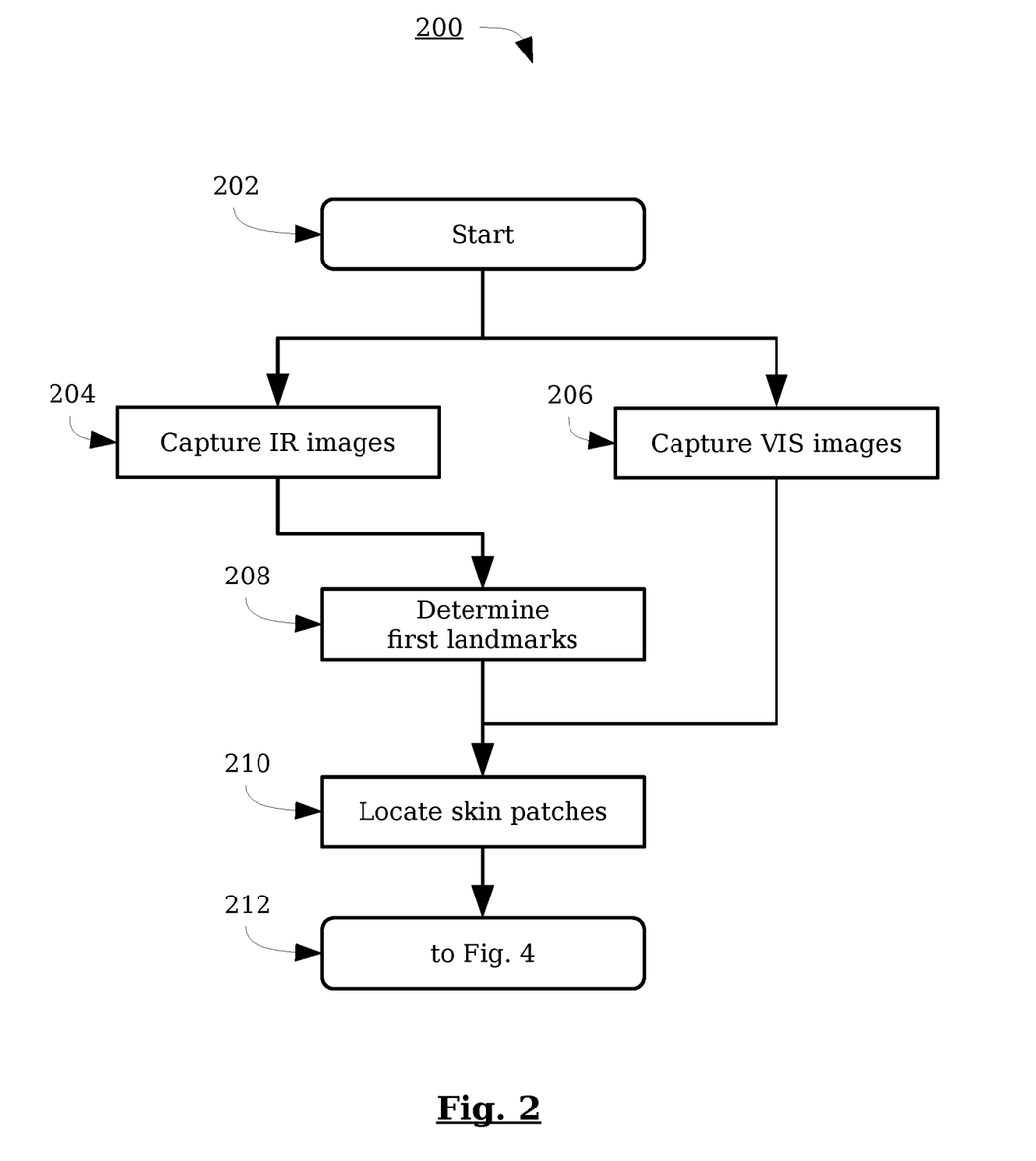
FIG. 2 depicts a flow chart of a method for locating one or more skin patches according to a first embodiment.

FIG. 2 depicts a flow chart of a method for locating one or more skin patches according to a first embodiment. The process begins, 202, when operation of the system, in particular operation of a vehicle to which the system is attached, is initiated, for example when the user is seated in the vehicle. Images of a user's face are captured, 204, by the infrared camera 102. At approximately the same time, one or more images are captured, 206, by the visible light camera. In an alternative embodiment, both cameras capture images continuously, so that each camera generates and image series. These image series are recorded simultaneously at least to the extent that their respective recording times overlap. However, full synchronization is possible and beneficial to make the step of locating the skin patches, more accurate. The IR images are used to determine the locations of the first landmarks. Subsequently, the positions of the skin patches on the VIS images are determined based on the first landmarks. This step also takes into account the difference in position and angle of the cameras. In particular, the first landmarks may be transformed into a frame of reference of the VIS camera, as detailed below. Once the skin patches are located, the method continues by determining the heart beat features as described with reference to FIG. 4.

Figure 3:
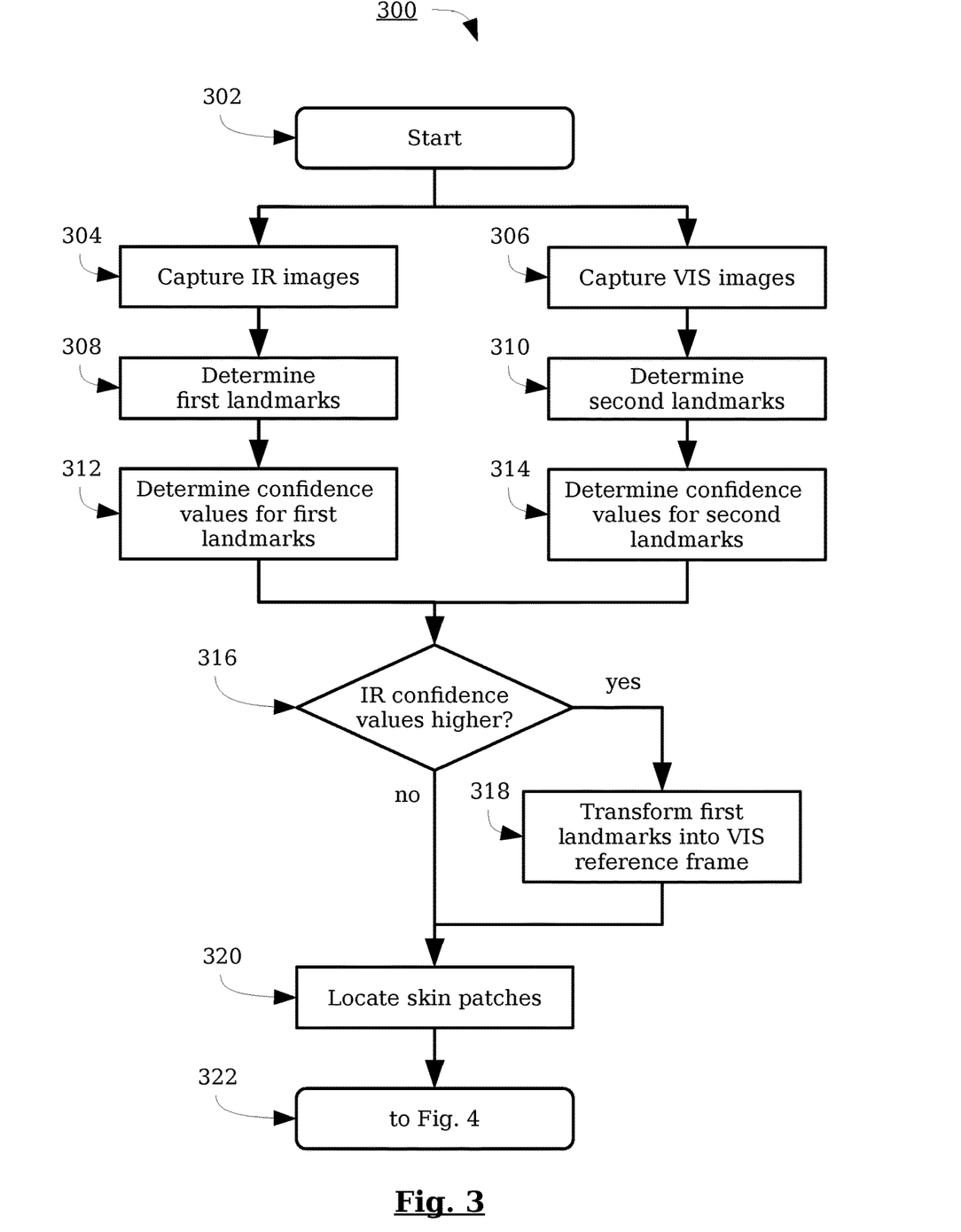
FIG. 3 depicts a flow chart of a method 300 for locating one or more skin patches according to a second embodiment.

FIG. 3 depicts a flow chart of a method 300 for locating one or more skin patches according to a second embodiment. Series of IR images and VIS images are captured, 304, 306, with a temporal overlap as described above. On both image series, the first and second landmarks are determined, 308, 310, and corresponding confidence values are determined, 312, 314. If a comparison, 316, yields higher confidence for the confidence values generated from the IR images, 316, the face landmarks from the IR camera are used. This may be, for example, the case when the system is used by the driver of a vehicle at natural lighting, and natural lighting is limited due to meteorological conditions and/or twilight. In that case, IR images may still have a sufficiently high signal-to-noise ratio for determining the first landmarks, in particular when the face is illuminated in the infrared, which does not distract the driver. In this case, the first landmarks are transformed into a reference frame of the VIS camera. In the next step, the locations of the skin patches are then determined, 320, using the first or second landmarks, whatever exhibits higher confidence. Once the positions of the patches are determined, the method is continued in FIG. 4.

Figure 4:
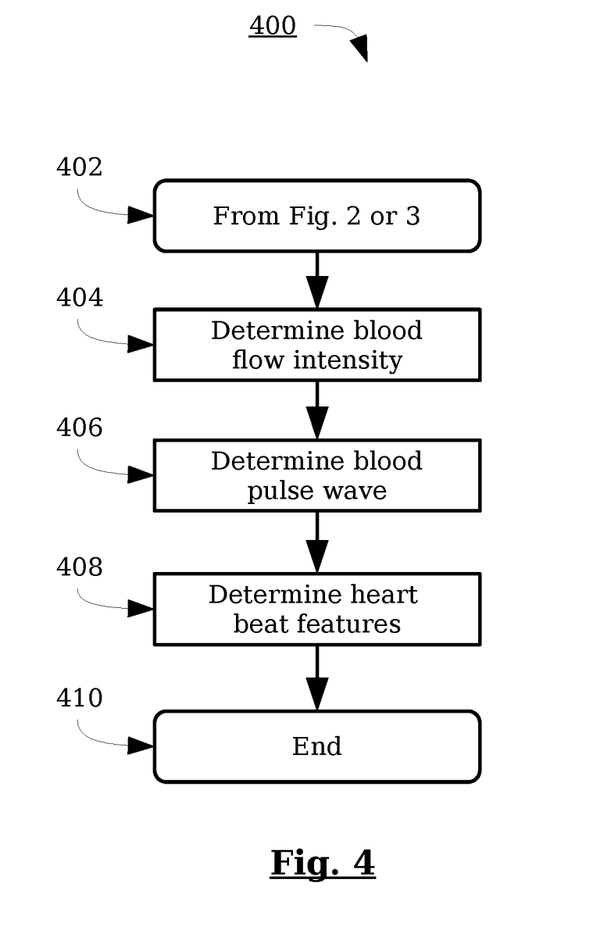
FIG. 4 depicts a flow chart of a method 400 for determining one or more heart beat features based on the skin patch positions.

FIG. 4 depicts a flow chart of a method 400 for determining one or more heart beat features based on the skin patch positions. As indicated in 402, method 400 uses the output generated in methods 200 and 300. Based on the skin patch values, a blood flow intensity is determined, 404. This step comprises extracting a channel suitable for the determination of a blood flow from the image, and applying predefined corrections to the image, such as noise reduction, and averaging over a plurality of pixels. As is the case with methods 200 and 300, the steps of method 400 are applied to each single image up to this point. The following steps 406-410, however, comprise analysis of a series of images. This series may be chosen in the same or in a different way as the series chosen for determining if to choose the first or second landmarks in step 316. As data are analyzed "live", while the images are recorded, the series may, for example, comprise a sliding window, i. e. overlapping series, so that blood flow intensity values from the same image are re-used, in order to reduce fluctuations in the output values for the heart beat features. At 406, a blood pulse wave is determined from a series of blood flow intensity values, based on, e. g. the series of images mentioned above. From the blood pulse wave, heart beat features are determined, 408. In particular, a heart rate, heart rate variability, or an interbeat interval may be determined, e. g., by determining peaks with a search algorithm, or a Fourier or wavelet transform. Once this final output is obtained, the analysis of a given image series ends at 410. However, the computing device 110 analyzes data generated from subsequent images continuously.

REFERENCE SIGNS

100 System for locating one or more skin patches
102 IR camera
104 IR illumination
106 VIS camera
108 VIS camera settings storage
110 Computing device
112 IR landmark detector
114 IR confidence value calculator
116 VIS landmark detector
118 VIS confidence value calculator
120 IR landmark transformer
122 Skin patch locator
124 Skin patch analyzer
126 Pulse wave generator
128 Heart rate detector
200 Method for locating one or more skin patches
202-212 Steps of method 200
300 Method for locating one or more skin patches
302-322 Steps of method 300
400 Method for determining one or more heart beat features
402-410 Steps of method 400

The invention claimed is:

1. A system for determining one or more heart beat features, the system comprising:
   a visible light camera;
   an infrared camera; and
   a computing device;
   wherein:
   the visible light camera is operable to capture a series of visible light images of a face of a user;
   the infrared camera is operable to capture, during capturing the series of the visible light images, at least one infrared image of the face; and
   the computing device implemented in hardware is operable to:
   detect, on the at least one infrared image, one or more first face landmarks;
   detect, on at least one of the visible light images, one or more second face landmarks;
   determine a first confidence value of the one or more first face landmarks;
   determine a second confidence value of the one or more second face landmarks, wherein the second confidence value is expressed on the same scale as the first confidence value;
   compare the first confidence value to the second confidence value;
   in response to the first confidence value being greater than the second confidence value, determine a location of one or more skin patches on the series of visible light images based on the one or more first face landmarks;

in response to the second confidence value being equal to or greater than the first confidence value, determine the location of the one or more skin patches on the series of visible light images based on the one or more second face landmarks; and determine the one or more heart beat features based on the determined location of the one or more skin patches.

2. The system of claim 1, wherein the second confidence value is indicative of a confidence of the one or more second face landmarks on one of the one or more visible light images relative to a confidence of the one or more first face landmarks on one of the at least one infrared image.

3. The system of claim 1, wherein the second confidence value is indicative of a confidence of the one or more second face landmarks on a sequence of visible light images of the one or more visible light images relative to a confidence of the one or more first face landmarks on a sequence of infrared images of the at least one infrared image.

4. The system of claim 1, wherein, to determine the location of the one or more skin patches on the series of visible light images based on the one or more second face landmarks, the computing device is further operable to transform the one or more first face landmarks into a reference frame of the visible light camera.

5. The system of claim 1, wherein determining the one or more heart beat features comprises determining a blood flow intensity value.

6. The system of claim 1, wherein determining the one or more heart beat features comprises determining a blood pulse wave.

7. The system of claim 6, wherein the blood pulse wave is determined by remote photoplethysmography (rPPG) based on a time series of values obtained from the one or more visible light images.

8. The system of claim 1, wherein determining the one or more heart beat features comprises determining one or more of a heart inter-beat interval, a heart rate, and a heart rate variability.

9. The system of claim 1, wherein detecting the one or more first face landmarks comprises:

detecting, on a first infrared image, one or more first preliminary face landmarks;

detecting, on a second infrared image recorded before or after the first infrared image, one or more second preliminary face landmarks; and determining the one or more first face landmarks by interpolating between the one or more first preliminary face landmarks and the one or more second preliminary face landmarks.

10. The system of claim 1, wherein a frame rate of the visible light camera is equal to a frame rate of the infrared camera.

\* \* \* \* \*